United States Patent [19]

Andrews et al.

[11] Patent Number: 5,328,449
[45] Date of Patent: Jul. 12, 1994

[54] WOUND DRESSING FOR THE HANDS

[75] Inventors: Warren L. Andrews, Chicago; C. Robert Hammett, Palatine, both of Ill.

[73] Assignee: Wells LaMont, Niles, Ill.

[21] Appl. No.: 978,556

[22] Filed: Nov. 19, 1992

[51] Int. Cl.$^5$ .................... A61F 13/00; A61F 15/00; A61L 13/00
[52] U.S. Cl. ........................ 602/42; 602/43; 602/58; 602/21; 602/62; 604/292; 2/161.7; 2/917
[58] Field of Search .............. 602/21, 41, 42, 43, 602/47, 58, 62, 63, 64; 604/292, 306; 2/16, 21, 19, 159, 161 A, 164, 161.1, 161.2, 161.3, 161.4, 161.5, 161.6, 161.7, 161.8

[56] References Cited

U.S. PATENT DOCUMENTS

| | | |
|---|---|---|
| 1,507,153 | 9/1924 | Binns . |
| 2,251,027 | 7/1941 | Baker . |
| 2,549,660 | 4/1951 | Buhl et al. . |
| 2,916,036 | 12/1959 | Sutton . |
| 3,116,732 | 1/1964 | Cahill . |
| 3,119,118 | 1/1964 | Beebe . |
| 3,298,368 | 1/1967 | Charos . |
| 3,307,545 | 3/1967 | Surowitz ............... 128/156 |
| 3,327,705 | 6/1967 | Miller et al. . |
| 3,342,182 | 9/1967 | Charos . |
| 3,347,233 | 10/1967 | Migliarese . |
| 3,372,401 | 3/1968 | Woodward . |
| 3,384,083 | 5/1968 | Cozza et al. .............. 604/292 |
| 3,430,265 | 3/1969 | Mazza . |
| 3,473,699 | 10/1969 | Pike . |
| 3,504,379 | 4/1970 | Glick . |
| 3,521,631 | 6/1970 | Gardner et al. ............. 602/42 |
| 3,588,917 | 6/1971 | Antonious . |
| 3,881,197 | 5/1975 | Andrews . |
| 4,123,803 | 11/1978 | Rinehart . |
| 4,430,759 | 2/1984 | Jackrel .................. 2/164 |
| 4,476,588 | 10/1984 | Long . |
| 4,485,917 | 12/1984 | Smith . |
| 4,594,736 | 6/1986 | Connelly . |
| 4,638,796 | 1/1987 | Sims . |
| 4,725,279 | 2/1988 | Woodroof . |
| 4,767,619 | 8/1988 | Murray . |
| 4,775,372 | 10/1988 | Wilberg . |
| 4,783,857 | 11/1988 | Suzuki ................... 2/168 |
| 4,853,978 | 8/1989 | Stockum . |
| 4,971,047 | 11/1990 | Kanzler et al. . |
| 5,058,209 | 10/1991 | Eisenberg . |
| 5,058,573 | 10/1991 | Hess et al. . |
| 5,117,509 | 6/1992 | Bowers ................. 2/161 A |

OTHER PUBLICATIONS

Smith, et al., "Biosynthetic compound dressings-management of hand burns", Burns 14:405-408 (1988), Great Britain.

Primary Examiner—Paul Prebilic
Attorney, Agent, or Firm—McDermott, Will & Emery

[57] ABSTRACT

A medical glove or dressing for covering a wound, lesion, burn or similar injury to the hand is disclosed. The glove comprises a back portion, a palm portion and thumb and finger portions with adjustable opening and closure means for easy insertion of the hand and adjustable fitting of the glove without further trauma to the hand. The glove further comprises a material having at least three layers comprising: (a) a first inside layer which comprises a porous polyethylene film which enables moisture to be wicked away from the hand; (b) a second middle layer comprising an absorbent material for absorbing the moisture from the first layer; and (c) a third outer layer comprising a flexible, water-proof breathable material.

11 Claims, 1 Drawing Sheet

U.S. Patent  July 12, 1994  5,328,449
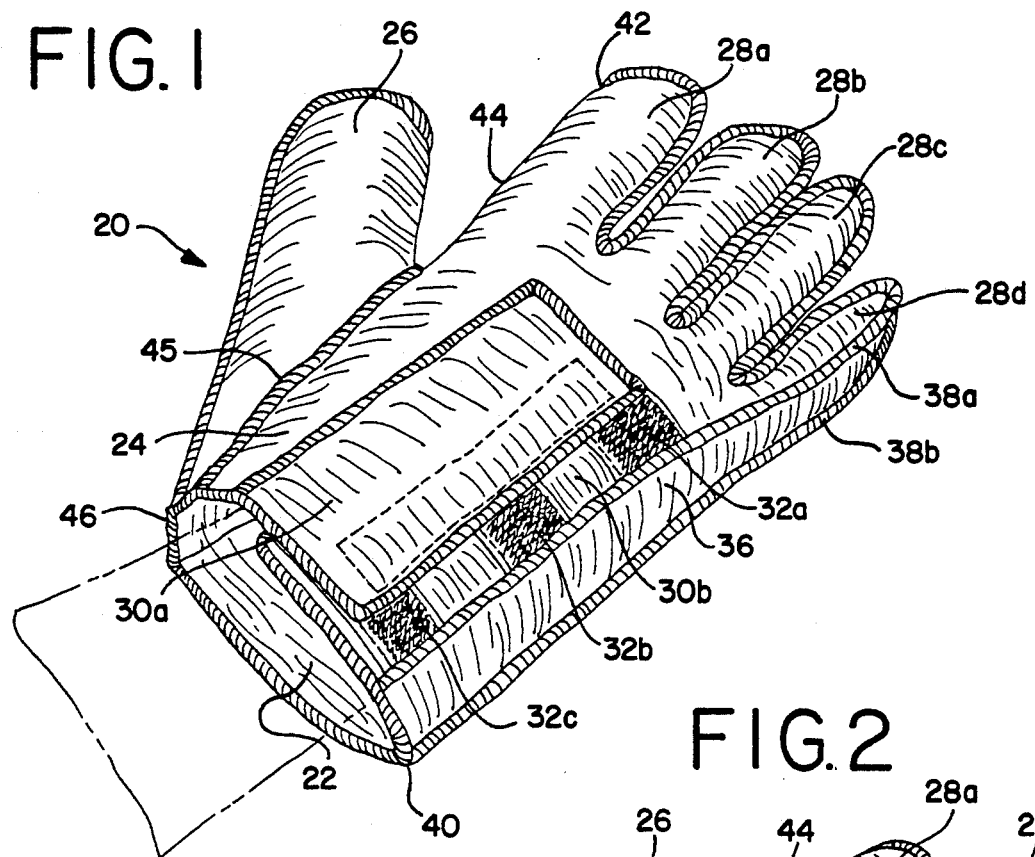
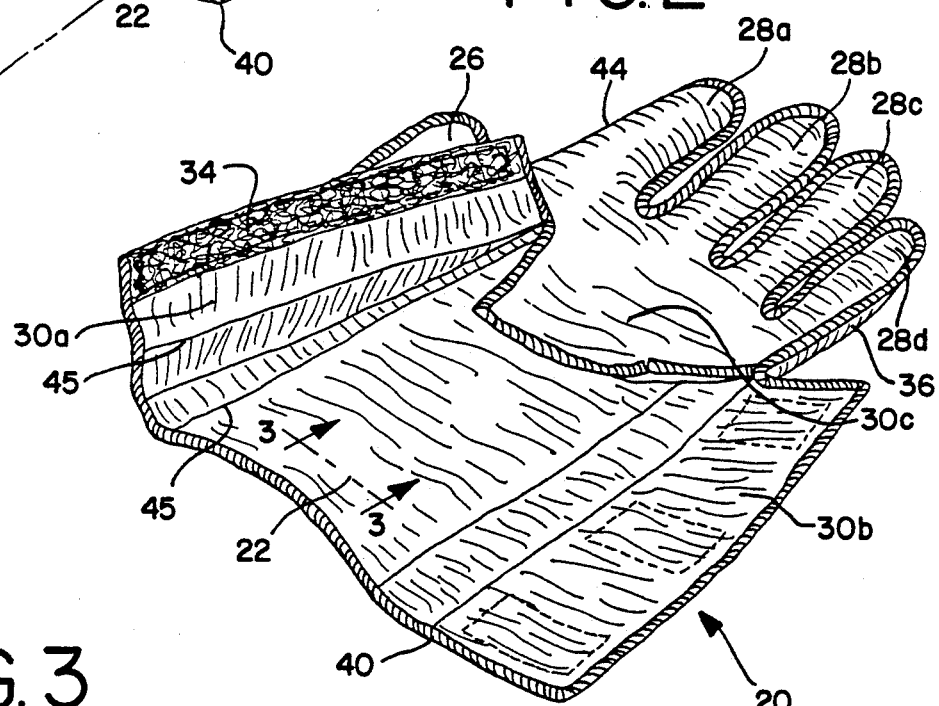
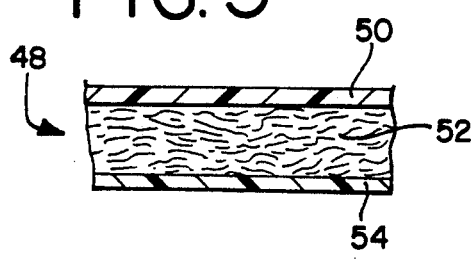

WOUND DRESSING FOR THE HANDS

FIELD OF THE INVENTION

This invention relates to medical gloves or dressings for the hands of a person having a wound, lesion, burn or similar injury, and particularly to medical gloves or dressings for the hands of burn patients.

BACKGROUND

Patients having wounds, lesions, burns or other similar trauma or injury to the hands require special treatment to preserve the function of the hand while promoting healing of the injury. According to Smith et al., Burns 14, (5): 405-408, (1988), six principles have been formulated for the care of burned hands to achieve the return of optimal function, including: (1) to do no harm; (2) to maintain vascularity; (3) to prevent infection; (4) to obtain wound closure; (5) to preserve and regain motion; and (6) to obtain optimal functional rehabilitation.

While various materials and methods of manufacturing gloves are known in the art, these materials and methods are not generally applicable to medical gloves used to cover an injured hand. For example, in one method, gloves are made by cutting two complimentary, flat, top and bottom hand-shaped sections and sewing them together around the perimeter, leaving an opening at the wrist end. One problem with using this type of glove to cover an injured hand is that the glove does not provide for an easy and comfortable insertion or removal of the hand. Further, gloves of this instruction do not allow comfortable movement of the injured hand, which could be harmful to return of optimal hand function.

Prior art medical gloves or hand dressings have attempted to avoid the above-described problems by enlarging the overall size of the glove so that the opening is wide enough to insert the hand and provide a loose fit. However, one problem with such an over-sized glove construction is that the loose fit causes the glove or dressing to slip off the hand. Also, the over-sized glove construction may cause loss of hand coordination and manipulation skills. For example, the excess material of an over-sized glove may make it difficult to handle small objects such as writing instruments or eating utensils.

It is therefore an object of the present invention to provide a medical glove for covering or dressing hands having wounds, lesions, burns or similar injuries, which facilitates easy insertion and removal of the hand and a comfortable fit, while still enabling a simple glove construction. It is another object to provide a medical glove or dressing which provides optimal hand coordination and manipulation functions and return of optimal hand function to a burn or other trauma patient. It is a further object to provide a medical glove made from a unique material which facilitates healing of the injured hand.

SUMMARY OF THE INVENTION

The above objects are accomplished by the present invention, which is a medical glove for covering wounds, lesions, burns or similar injuries to a hand comprising a back portion, a palm portion and thumb and finger portions for covering the hand. The medical glove has adjustable opening and closure means for easy insertion and removal of the hand and for adjustably fitting the glove to the hand. The glove further comprises a material having at least three layers comprising:

(a) a first inner layer which will come into contact with the hand comprising a porous polyethylene film which enables moisture to be wicked away from the hand and is non-adherent so the glove will not stick to the wound;

(b) a second middle layer comprising an absorbent material for absorbing the moisture from the first layer; and (c) a third outer layer comprising a flexible waterproof breathable material.

BRIEF DESCRIPTION OF THE DRAWINGS

FIG. 1 is a perspective view of a back side of a medical glove according to the invention, showing adjustable opening and closure means in a closed position;

FIG. 2 is another perspective view of the glove of FIG. 1, showing the adjustable opening and closure means in an open position; and FIG. 3 is a sectional view along line 3—3 of FIG. 2.

DETAILED DESCRIPTION OF THE INVENTION

As shown in FIGS. 1 and 2, in one preferred embodiment, a medical glove 20 in accordance with the present invention comprises a palm portion 22, a back portion 24, a thumb portion 26, and finger portions 28a–d. The glove 20 further comprises adjustable opening and closure means which, in the preferred embodiment, comprises at least two adjustable opening and closure flaps 30a and b. The adjustable opening and closure flaps 30a and b have adjustable fastening means, for example, hook and loop fasteners such as horizontal Velcro strips 32a–c and vertical mating Velcro strip 34. Other adjustable fasteners which are well known in the art may be substituted for the Velcro fasteners so long as the selected fasteners enable adjustable opening and closing of the glove for various sized hands and a comfortable fit. The adjustable opening and closure means enables easy and comfortable insertion and removal of an injured hand when the adjustable opening and closure means is in an open position (FIG. 2), while also allowing for quick and easy adjustment of a comfortable fit of the medical glove 20 (FIG. 1). The adjustable opening and closure means also enables a treating medical clinician to easily inspect or treat the injured hand.

In the embodiment shown in FIGS. 1 and 2, the adjustable opening and closure means is integral with and forms a portion of the back portion 24. However, it should be understood that in another preferred embodiment, the adjustable opening and closure means may be integral with and form a portion of the palm portion 22.

The adjustable opening and closure means of the preferred embodiment further comprises an additional flap 30c which tucks under the opening and closure flaps 30a and b to insure complete coverage of the hand, while preventing any exposure of the hand to the atmosphere. Such exposure could cause infection or further trauma to the injured hand.

In order to provide a comfortable fit, in the preferred embodiment of the invention, the finger portions 28a–d comprise palm-side finger portions which are integral with and form one continuous piece with back portion 24, as shown in FIGS. 1 and 2, and palm-side finger portions (not shown) which are integral with and form one continuous piece with the palm portion 22. The back-side finger portions are an approximate mirror image of the palm-side finger portions. The palm- and back-side finger portions are joined to form finger portions 28a–d by continuous connecting piece 36 which is attached to the back portion 24 and the palm portion 22 at seams 38a and b. The continuous connecting piece 36 connects the back portion 24 to the palm portion 22 and finger portions 28a–d from the outer wrist end 40 of the glove all the way to the tip 42 of the index finger portion 28a.

At the opposite side of the glove below the tip 42 of the index finger portion 28a, a fold 44 is formed where the back portion 24 and palm portion 22 are one continuous piece. The remaining portion of the glove below the fold 44 is completed by thumb portion 26 which connects the back portion 24 and the palm portion 22 of the glove by V-shaped thumb opening seam 45.

Those skilled in the art will readily recognize that the palm, back, finger and thumb portions of the medical glove of the invention can be made of other constructions so long as an adjustable opening and closure means is provided for easy and comfortable insertion and removal of a hand, while enabling an adjustable, comfortable fit. Also, the preferred glove construction of the invention will enable optimal protection of an injured hand, while providing for maximum function of the hand such as manipulation of small objects and comfortable movement of the hand. For example, in another embodiment of the invention, a medical glove may comprise a continuous connecting piece such as connecting piece 36 which connects the entire outer perimeter of the glove from one side of the wrist end 40 to the opposite side at wrist end 46 of the thumb portion 26. In yet another embodiment of the invention, the medical glove may comprise adjustable opening and closure means on the palm portion of the glove.

The medical glove of the present invention is constructed of a unique material having at least three layers which enable optimal healing of an injured hand such as a burned hand. As shown in FIG. 3, this unique material 48 comprises a first, inner layer 50, which will contact the injured hand or any medicament or material previously applied to the hand. This inner layer 50 comprises a porous, non-adherent polyethylene film which enables moisture to be wicked away from the injured hand and prevent adhesion of the glove to the wound.

In a preferred embodiment, the inner layer 50 comprises a porous polyethylene film having a thickness of about 3.5–5.0 mils. One example of a most preferred material for the inner layer 50 is a polyethylene film sold by Applied Extrusion Technologies, Middletown, Del., under the trademark P530 Delnet. This material has a thickness of about 3.8–4.8 mils, a boss count (MD) of about 18–24 ct/in, a boss count (CD) of about 32–40 ct/in and a yield of about 25–35 syd/lb.

The inner layer 50 is hydrophobic and facilitates wicking of any liquid discharge from a hand injury such as a burn to the glove's middle layer 52, which results in a drier surface adjacent to the skin. The inner layer 50 also prevents adhesion of the glove to the wound. In use of the glove, when an injured hand has any fluid discharge, the fluid will pass through the inner layer 50, saturate the middle layer 52 and migrate by wicking toward the outer layer 54, leaving a relatively dry surface at the hydrophobic inner layer 50 adjacent the hand.

The second, middle layer 52 comprises an absorbent material for absorbing any moisture from the inner layer 50. In a preferred embodiment, the middle layer 52 comprises an absorbent needle-punched, non-woven rayon such as a four ounce per square yard needle-punched, non-woven rayon. Other suitable absorbent materials include creped cellulose wadding, an airfelt of airlaid pulp fibers, cotton or other well known absorbent materials used in wound dressings.

A third, outer layer 54 comprises a flexible, waterproof and breathable material which protects the hand from exposure to contaminants from the outer atmosphere, while preventing leakage of any moisture from the injured hand. In a preferred embodiment of the invention, the outer layer 54 comprises a waterproof, breathable polyurethane film of approximately 1 mil thickness. Other suitable waterproof, breathable outer layer materials include polypropylene or polyethylene such as a low density, opaque polyethylene film, or other waterproof breathable materials commonly used in the art of wound dressings.

The layers 50, 52, 54 can be secured to one another in any convenient manner; for example, the layers can be sewn together, adhesively secured or bonded with heat and pressure or sonics.

The medical glove of the invention has many advantages. First, the glove can be comfortably applied over an injured hand without causing further trauma. Second, the glove can be adjustably fitted to accommodate different sized hands and various types of injuries. Third, the glove enables any fluid discharge to be wicked away from the injured hand which can help prevent infection and promote healing. Fourth, the inner layer of the glove prevents adhesion to the wound. Fifth, the glove enables good manipulation of the hand which is important to the return of full functional skills. Sixth, the glove provides a comfortable protection of the injured hand from the outer environment while preventing leakage of any fluid from the injured hand. Seventh, the glove enables inspection or treatment of a wound without removal of the glove.

While the medical glove of the invention has been described with respect to specific embodiments, many modifications may be made without departing from the spirit and scope of the invention.

What is claimed is:

1. A medical glove for covering a wound, lesion, burn or similar injury to a hand comprising a back portion, a palm portion, and thumb and finger portions; said glove having adjustable opening and closure means enabling easy insertion and removal of said hand, adjustable fitting of said glove to said hand, and easy inspection or treatment of said hand without requiring removal of said glove; said glove further comprising a material having at least three layers comprising:
   (a) a first inner layer adapted to be adjacent to said hand comprising a porous polyethylene film which is non-adherent to said wound and which enables moisture to be wicked away from said hand;
   (b) a second middle layer comprising an absorbent material for absorbing the moisture from said first layer; and
   (c) a third outer layer comprising a flexible, waterproof, breathable material which protects the hand from exposure to contaminants from the outer atmosphere while preventing leakage of moisture from said hand.

2. The medical glove of claim 1 wherein said adjustable opening and closure means comprises at least two adjustable opening and closure flaps having adjustable fastening means thereon.

3. The medical glove of claim 2 wherein said adjustable fastening means comprises mating hook and loop fasteners.

4. The medical glove of claim 1 wherein said adjustable opening and closure means is integral with and forms a portion of said back portion.

5. The medical glove of claim 1 wherein said adjustable opening and closure means is integral with and forms a portion of said palm portion.

6. The medical glove of claim 1 wherein said porous polyethylene film has a thickness of about 3.5–5.0 mils.

7. The medical glove of claim 1 wherein said second middle layer comprises an absorbent needle-punched, non-woven rayon.

8. The medical glove of claim 1 wherein said third outer layer comprises a waterproof, breathable polyurethane film.

9. The medical glove of claim 8 wherein said polyurethane film has a thickness of about 1 mil.

10. The medical glove of claim 1 wherein said first, second and third layers are adhesively secured together.

11. A medical glove for covering a wound, lesion, burn or similar injury to a hand comprising a back portion, a palm portion, and thumb and finger portions; said glove having adjustable opening and closure means comprising at least two adjustable opening and closure flaps having adjustable fastening means for facilitating insertion and removal of said hand, adjustable fitting of said glove and inspection of said hand without requiring removal of said glove; said glove further comprising a material having at least three layers comprising:

(a) a first inner layer adapted to be adjacent to the hand comprising a porous, non-adherent polyethylene film of about 3.5–5.0 mils thickness which enables moisture to be wicked away from the hand;

(b) a second middle layer for absorbing moisture from said first layer comprising an absorbent needle-punched, non-woven rayon; and (c) a third outer layer comprising a flexible, waterproof and breathable polyurethane film of about 1 mil thickness.

* * * * *